(12) United States Patent
Darling, Jr.

(10) Patent No.: US 6,213,986 B1
(45) Date of Patent: Apr. 10, 2001

(54) LIQUID FLOW RATE CONTROL DEVICE

(75) Inventor: Phillip H. Darling, Jr., Fullerton, CA (US)

(73) Assignee: Appro Healthcare, Inc., Buffalo, NY (US)

(*) Notice: Subject to any disclaimer, the term of this patent is extended or adjusted under 35 U.S.C. 154(b) by 0 days.

(21) Appl. No.: 08/980,461

(22) Filed: Nov. 28, 1997

Related U.S. Application Data

(63) Continuation-in-part of application No. 08/674,552, filed on Jul. 1, 1996, now Pat. No. 5,730,730.
(60) Provisional application No. 60/004,634, filed on Sep. 29, 1995.

(51) Int. Cl.[7] .................................................. A61M 5/00
(52) U.S. Cl. ........................ 604/248; 604/254; 604/256; 137/423; 137/430
(58) Field of Search .................................. 604/251–256, 604/246, 248; 137/423, 430

(56) References Cited

U.S. PATENT DOCUMENTS

| | | |
|---|---|---|
| 1,235,316 | 7/1917 | Henderson . |
| 2,374,076 | 4/1945 | Burckhardt . |
| 2,665,706 | 1/1954 | Hansen . |

(List continued on next page.)

FOREIGN PATENT DOCUMENTS 2282278  8/1974  (FR) .

Primary Examiner—Mark Bockelman
(74) Attorney, Agent, or Firm—Howard R. Lambert

(57) ABSTRACT

A fluid flow rate control device, especially adapted for controlling the flow of IV fluid to a patient, comprises a first vented fluid chamber having an upper fluid inlet end with a hollow spike which enables fluid connection with a conventional fluid container. A free floating float valve in the first chamber blocks the flow of fluid into the first chamber from the fluid container according to whether or not the fluid level in the first chamber is at a preestablished fluid level, thereby providing a constant pressure head regardless of fluid level in the fluid container. A lower end of the first chamber is connected, through a flow regulator, such as a screw-type valve, to an upper inlet end of a second, vented, drip chamber, the lower end of which is adapted for connection to a discharge tube, such as an IV tube. A second, free floating float valve in the second chamber blocks the flow of fluid from the second chamber into the discharge tube when the fluid level in the second chamber is at or below a preestablished minimum level and blocks flow of fluid into the second chamber when the fluid level in the second chamber reaches a preestablished maximum level. A first variation fluid flow control device is disclosed in which the first an second chambers are arranged in a side-by side configuration and a second variation fluid flow control device is disclosed in which fluid flow through the device is controlled in response to relative rotation between axially-aligned upper and lower shell segments of the device.

5 Claims, 5 Drawing Sheets

U.S. PATENT DOCUMENTS

| | | |
|---|---|---|
| 2,850,211 | 9/1958 | Fernandez . |
| 2,854,992 | 10/1958 | Hewitt . |
| 3,001,397 | 9/1961 | Leonard . |
| 3,034,504 | 5/1962 | Winsor . |
| 3,123,094 | 3/1964 | Toschkoff . |
| 3,216,418 | 11/1965 | Scislowicz . |
| 3,216,419 | 11/1965 | Scislowicz . |
| 3,323,550 | 6/1967 | Lee . |
| 3,323,774 * | 6/1967 | Wilson . |
| 3,468,308 | 9/1969 | Bierman . |
| 3,563,090 | 2/1971 | Deltour . |
| 3,566,897 | 3/1971 | Collier . |
| 3,581,754 | 6/1971 | Adams . |
| 3,587,313 | 6/1971 | Smith . |
| 3,667,464 | 6/1972 | Alligood, Jr. . |
| 3,731,681 | 5/1973 | Blackshear . |
| 3,738,361 | 6/1973 | Price . |
| 3,744,492 | 7/1973 | Leibinsohn . |
| 3,890,968 | 6/1975 | Pierce . |
| 3,929,157 | 12/1975 | Serur . |
| 3,931,818 | 1/1976 | Goldowsky ..................... 128/214 |
| 3,989,043 | 11/1976 | Dimeff ............................. 128/214 |
| 4,043,332 | 8/1977 | Metcalf . |
| 4,096,879 | 6/1978 | Serur . |
| 4,142,523 | 3/1979 | Stegeman . |
| 4,143,659 | 3/1979 | Biedermann . |
| 4,186,740 | 2/1980 | Guerra . |
| 4,187,847 | 2/1980 | Loeser . |
| 4,191,208 | 3/1980 | Mylander . |
| 4,207,871 | 6/1980 | Jenkins . |
| 4,217,993 | 8/1980 | Jess . |
| 4,265,240 | 5/1981 | Jenkins . |
| 4,269,222 | 5/1981 | Palti . |
| 4,340,050 | 7/1982 | Noiles . |
| 4,375,813 | 3/1983 | Hessel . |
| 4,405,000 | 9/1983 | Fuller . |
| 4,436,090 | 3/1984 | Darling . |
| 4,474,574 | 10/1984 | Wolfe . |
| 4,496,351 | 1/1985 | Hillel . |
| 4,515,588 | 5/1985 | Amendolia . |
| 4,522,228 | 6/1985 | Campau . |
| 4,588,396 | 5/1986 | Stroebel . |
| 4,613,325 | 9/1986 | Abrams . |
| 4,789,000 | 12/1988 | Aslanian . |
| 4,802,506 | 2/1989 | Aslanian . |
| 4,807,660 | 2/1989 | Aslanian . |
| 4,857,048 | 8/1989 | Simons . |
| 4,863,437 | 9/1989 | Clarke . |
| 4,931,050 | 6/1990 | Idriss . |
| 4,976,687 | 12/1990 | Martin . |
| 5,019,047 | 5/1991 | Kriesel . |
| 5,033,714 | 7/1991 | Winchell et al. . |
| 5,104,750 | 4/1992 | Winchell et al. . |

* cited by examiner

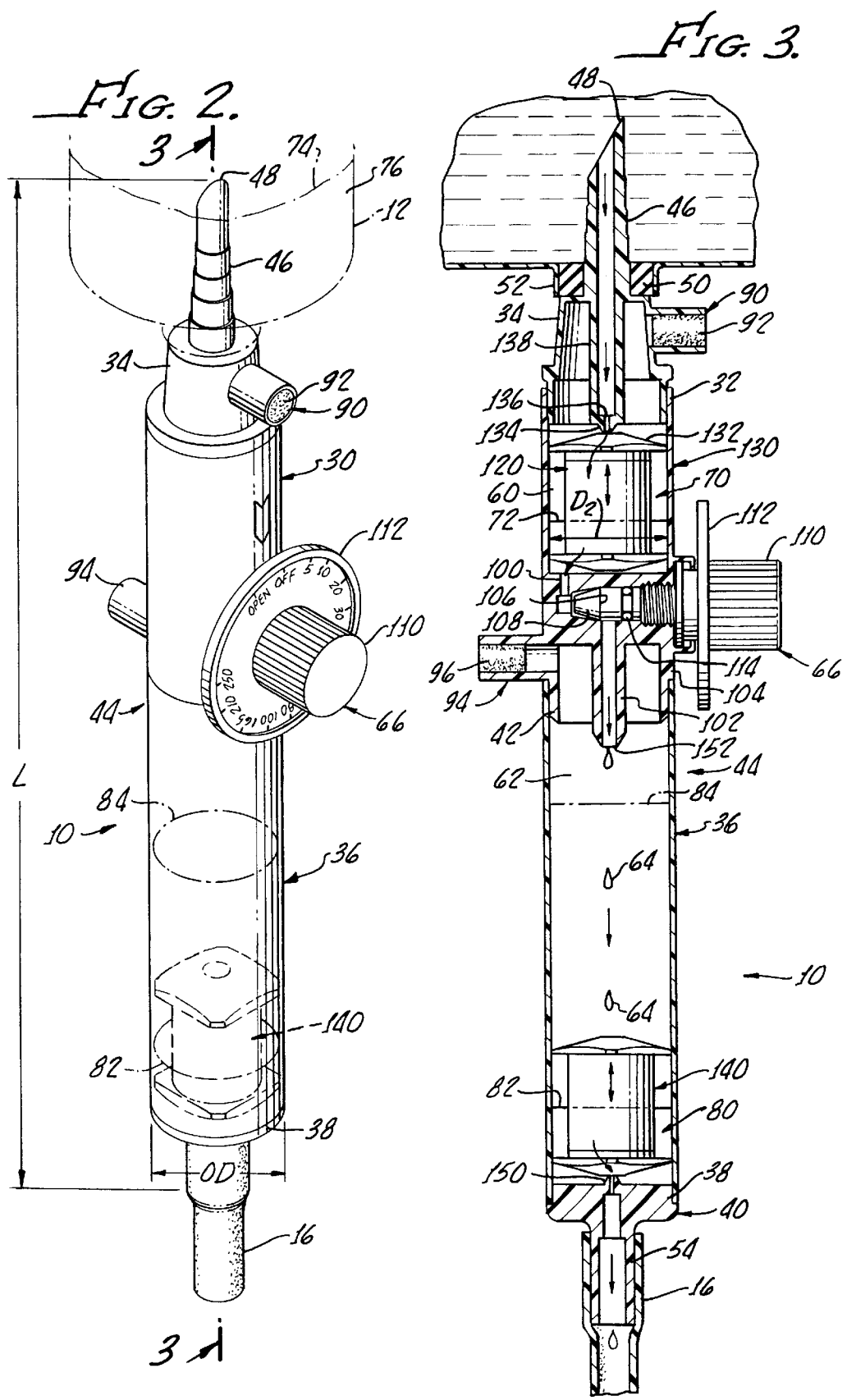

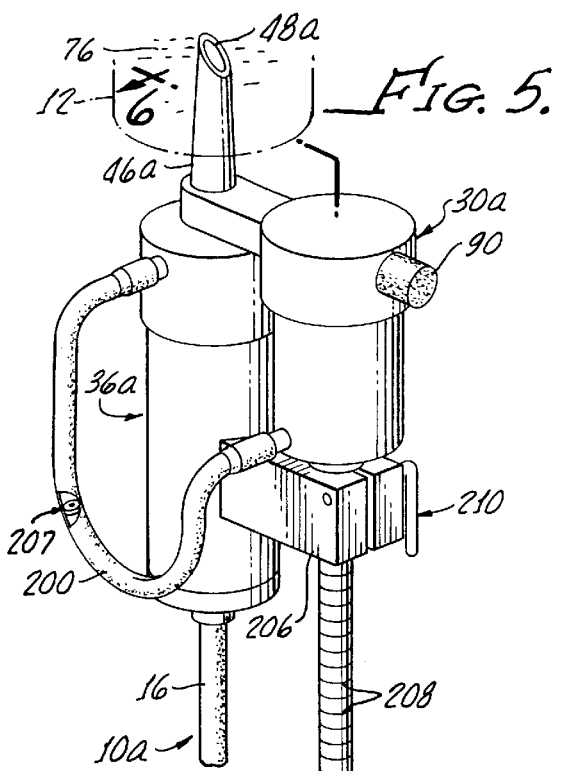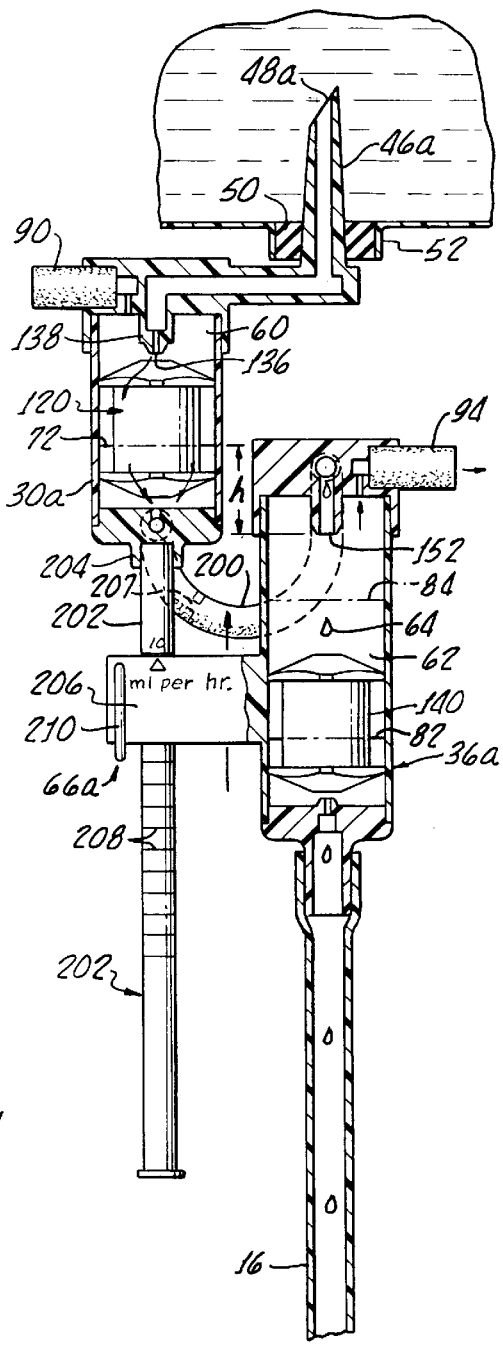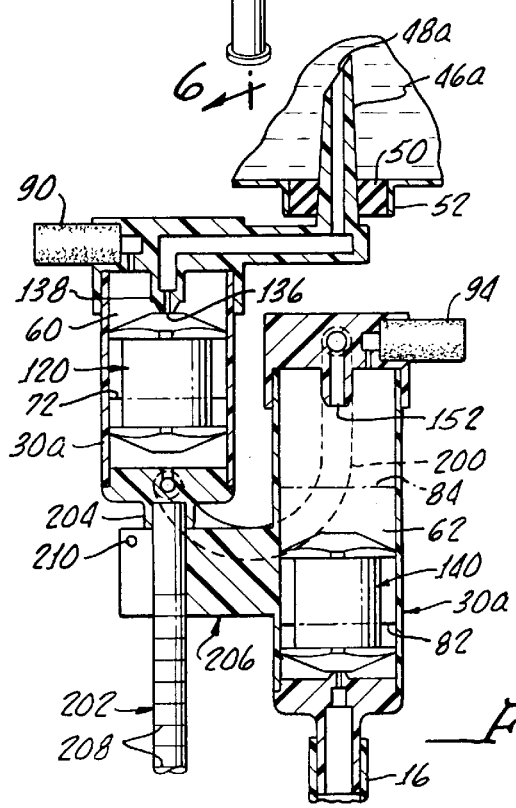

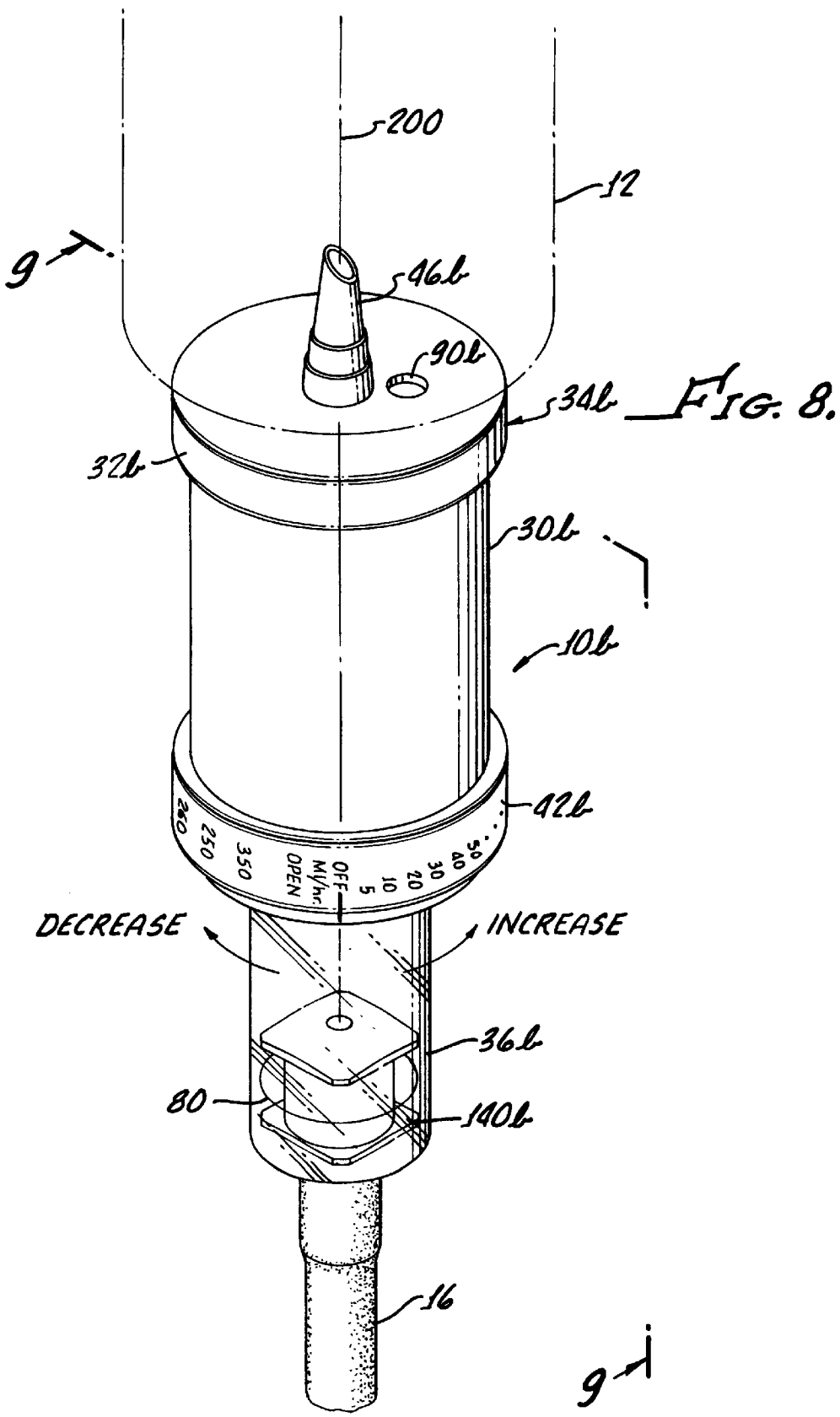

LIQUID FLOW RATE CONTROL DEVICE

This application is a continuation-in-part application of U.S. serial No. 08/674,552, filed Jul. 1, 1996 now U.S. Pat. No. 5,730,730, which claims the benefit of U.S. provisional application Ser. No. 60/004634, filed Sep. 29, 1995.

BACKGROUND OF THE INVENTION

1. Field of the Invention

The present invention relates generally to apparatus for controlling flow rates of liquids and, more particularly, to apparatus for maintaining accurate, precise and stable liquid flow rates in medical liquid delivery systems, such as intravenous (IV) fluid delivery systems.

2. Background Discussion

Many applications exist in which the precisely-controlled flow of small quantities of liquid materials is essential. One particularly critical example of such applications is the required precise delivery of controlled amounts of intravenous (IV) liquids to patients in hospitals, clinics, or in the field.

Gravity-driven IV liquid delivery systems or devices known to the present inventor utilize variable orifice flow control valves to control the flow rate of fluids to a patient undergoing treatment. Such known valves require a constant pressure drop, ΔP, across the orifice to maintain a stable, accurate and precise flow rate of fluid into patients to which the systems or devices are connected.

Some of these known flow control systems or devices utilize one or more fixed orifices and adjust the pressure drop, ΔP, across the orifice(s) to set the fluid flow rate. This pressure drop (the absolute sum of the positive and negative pressure) across the orifice(s) calibrated for a liquid of known viscosity and density determines the instantaneous fluid flow rate through the orifice(s).

Many known variable and fixed orifice fluid flow control systems attempt to circumvent or accommodate the normal decrease in positive fluid head pressure as the supply liquid level drops as, for example, liquid is drained from an IV bottle, and also variations in negative or suction pressure in the patient delivery line, as may, for example, be caused by patient movement or changes in the patient's venous pressure.

Variable orifice flow control valves of some known IV flow control devices are marked with flow rates that appear to assume an average pressure drop, ΔP, across the orifice, with no control of supply head pressure or patient line suction. For example, the fluid flow control valves disclosed in U.S. Pat. Nos. 4,789,000; 4,802,506 and 4,807,660 are considered representative of this type device. Instructions provided with commercial versions of the just-mentioned type of IV flow control devices caution users initially to count the number of liquid drops falling through an associated drip chamber in a prescribed period of time to establish an accurate flow rate, and thereafter to adjust the valve frequently to maintain a relatively constant liquid delivery rate as the supply liquid head and/or the patient line pressures changes.

Other known IV flow rate control systems, such as those disclosed in U.S. Pat. Nos. 3,929,157; 4,340,050 and 4,588, 396, disclose or suggest controlling fluid head pressure by transferring liquid from a primary liquid supply source into a secondary vessel in which the level is held constant and independent of the decreasing head pressure of the primary liquid source as it empties.

Other examples of known IV devices are disclosed in U.S. Pat. No. 3,929,157. These particular patents disclose IV devices in which a tube connects a rigid supply source to a secondary chamber for head pressure control. Liquid flows under gravity from the supply source into the secondary chamber until the bottom of the tube is covered. At that point air can no longer pass up the tube to displace the in-flowing liquid and flow stops. The region above the liquid in the secondary chamber is connected to the atmosphere (that is, the region is at atmospheric pressure), so there is no coupling through the air between the supply head pressure and the head pressure in the chamber.

The head pressure on a fixed outlet orifice located in the bottom of the secondary chamber determines the rate of flow, which may be adjusted by sliding the secondary chamber up or down on the tube from the supply source, thereby adjusting the head pressure of the liquid in the secondary chamber. A liquid collection chamber below the orifice collects the liquid and a flexible tube conducts the liquid from the collection chamber to a patient. This collection chamber is also vented to atmosphere so that changes in the liquid height in the patient line or changes in venous back pressure are uncoupled from the orifice and will have no effect on the flow rate through the orifice.

U.S. Pat. No. 4,340,050 discloses the use of a collapsible bag for the supply source. The bag discharges liquid into a liquid-receiving chamber which is vented to the atmosphere. A float-type valve is pivotally mounted in the liquid-receiving chamber for maintaining a constant liquid level. As disclosed, a second chamber, having fixed orifices at various heights and which is fluidly connected to the liquid-receiving chamber, can be moved up and down relative to the liquid-receiving chamber to vary the head pressure on the orifices. Liquid passing through the orifices collects in the bottom of the second chamber and is conducted to a patient through a flexible IV tube. This second chamber is vented to the atmosphere above the liquid on both sides of the orifices, thereby uncoupling the orifices from any pressure changes in the IV line connected to the patient.

In another example of the known IV flow control art, U.S. Pat. No. 4,588,396 discloses the use of a tube which connects a rigid supply source to a liquid-receiving chamber in which a constant liquid level is maintained in the manner disclosed in above-mentioned U.S. Pat. No. 3,929,157. The air above the liquid in the receiving chamber, which is the source of displacement air in the supply vessel, is vented to atmosphere through a metering valve which is used for flow rate control, instead of an orifice being used in the IV liquid path. Liquid is disclosed as flowing out of this collection chamber through a sealed drip chamber which is connected to a patient delivery line. It appears, however, that changes in the height of the liquid in the patient line will couple through the air in the sealed drip chamber to the liquid in the collection chamber and affect the flow rate through the system.

Other known IV flow rate control systems, such as are disclosed in U.S. Pat. Nos. 4,142,523; 4,186,740; 4,515,588 and 4,863,437, use a diaphragm or collapsible chamber which adjusts a flow control orifice or passage to minimize flow rate changes caused by supply head pressure and patient delivery line pressure variations. As far as the present inventor is aware, however, none of such disclosed IV devices isolate the flow control element from both the supply head and patient line pressure variations.

By way of a still further example, U.S. Pat. No. 4,613,325 discloses an IV flow rate control system that amplifies and uses a velocity dependent pressure drop across a restriction in the flow path to modulate the size of an upstream variable orifice flow control. There does not, however, appear to be disclosed any means for isolating the flow restriction from supply head or patient line pressure variations.

Further examples of known IV flow control devices are disclosed in U.S. Pat. Nos. 5,014,750 and 5,033,714. These patents disclose a pressurized constant pressure liquid supply that is fed through an adjustable flow restricter into a patient delivery line, the entire IV system being worn by the patient. However, since the system is tied to the patient, little variation would be expected in patient line pressure except that caused by venous blood pressure.

Many of the known IV flow rate control devices that attempt to compensate for changes in supply head pressure and patient line pressure are expensive and complex, and the range of pressure compensation before a nurse must reset the flow rate is considered by the present inventor to be limited, particularly, since in a "worst case" situation a patient's line suction on the flow control orifice can, depending, for example, on the patient's position (e.g., standing, sitting or lying) increase by 30 to 40 cm of water, possibly doubling the pressure drop across the orifice.

An important need, therefore, still exists in the medical field for an improved, simple, reliable and relatively low-cost, gravity-driven IV system that delivers an accurate, precise and stable flow rate of medicinal liquid to patients, in bed or ambulatory, in hospital, home, field or transport settings. It is, therefore, a principle objective of the present invention to provide such an improved IV system.

SUMMARY OF THE INVENTION

In accordance with the present invention, there is provided a gravity flow fluid flow regulating device with constant fluid head provision that is particularly for regulating the flow of fluids, such as IV fluids, from a fluid source into a patient's body. The flow regulating device comprises a first, constant fluid head chamber having an upper fluid inlet end region and a lower, fluid outlet region. Included is a second, drip, chamber having an upper fluid inlet end region and a lower, fluid outlet end region, the lower fluid outlet end region being configured for having attached thereto a fluid delivery tube, such as a conventional IV fluid delivery tube for providing IV fluid into a patient's body.

Further comprising the present invention are fluid flow regulating means connected in fluid flow relationship between the fluid outlet end region of the first chamber and the fluid inlet end region of the second chamber, the regulating means being configured for regulating the gravity flow of fluid from the first chamber into the second chamber.

Further included are means enabling a fluid-flow connection between the fluid inlet end region of the first chamber and a lower, discharge region of a fluid source, such as a source of IV fluid that may be either open or closed to ambient pressure.

Still further included in the present flow control device are first, upper, fluid level control means disposed in the first chamber for causing, when the connecting means connect the first chamber to a preexisting source of fluid for receiving a flow of fluid therefrom, a preestablished fluid level to be substantially maintained in the first chamber as the fluid level in the source decreases.

In accordance with a preferred embodiment of the invention, the first, upper, fluid level control means include an inlet orifice at the fluid inlet end region of the first chamber and a first, upper, float valve disposed in a free-floating relationship inside the first chamber. The first, upper, free-floating valve is configured for blocking the inlet orifice to stop the gravity flow of fluid through the orifice from a connected source of fluid when the fluid level in the first chamber is at the preestablished level and for unblocking the inlet orifice to permit a gravity flow of fluid through the orifice from the fluid source when the fluid level in the first chamber falls below the preestablished level.

Also included in the present flow control device are first venting means located at an upper region of the first chamber above the preestablished fluid level therein for venting the first chamber to ambient surrounding pressure and second venting means located at an upper region of the second chamber for venting the second chamber to ambient surrounding pressure.

At least a side wall region of the second chamber is constructed of a transparent material so that a rate of fluid dripping through the second chamber can be observed by a user of the device.

Further, according to a preferred embodiment, the fluid flow regulating means comprise a valve body having a rotatably-mounted valve stem for incremental rotational movement between a first, fully-closed position which blocks the gravity flow of fluid from the first chamber into the second chamber and a second, fully-open position in which the gravity flow of fluid from the first chamber into the second chamber is at a maximum flow. The valve stem is disposed in the valve body for being manually set at any selected rotational position between the first and second positions so as to thereby enable a user of the device to selectively control the gravity flow of fluid from the first chamber into the second chamber. An indicator dial calibrated with respect to rotational positions of the valve stem may be provided for enabling a user to read fluid flow rates from the first chamber into the second chamber associated with different rotational positions of the valve stem.

A second, lower, flow control means comprises a second, lower float valve that is disposed in free-floating relationship inside the second chamber for closing the lower, fluid outlet end region when fluid in the second chamber falls to a preestablished lower level to prevent the inclusion of air from the outlet region of the second chamber, for example, into the fluid conduit to a patient's body and for alternatively closing the fluid inlet to the second chamber when the fluid in the second chamber rises to a preestablished upper lever.

In a variation of the fluid flow control device, the fluid flow regulating means of the flow control device comprise a flexible fluid conduit connected in fluid flow relationship between the outlet end region of the first chamber and the fluid inlet end region of the second chamber. In such configuration, means are included for selectively controlling the vertical distance between the preestablished fluid level in the first chamber and the fluid inlet region of the second chamber.

There is accordingly provided a fluid flow control device, particularly for use in an IV supply system, which, as an illustration, provides a constant fluid head as the fluid level in a source of IV fluid to which the device is connected decreases as the fluid is introduced through the device into a patient's body.

There is further provided another variation gravity flow IV fluid flow control device with constant fluid head provision which comprises an upper shell segment and a lower shell segment, a lower region of the upper shell segment being connected to an upper region of the lower shell segment for relative rotation between the upper and lower shell segments and for limited axial movement therebetween.

Included is a first, upper fluid chamber defined inside the upper shell segment, the upper shell segment having an upper end region configured for receiving a flow of IV fluid from an external IV fluid source into said first upper fluid chamber. A second, lower fluid chamber is defined in the lower shell segment, the lower shell segment having a lower end region configured for discharging the flow of IV fluid from the second, lower fluid chamber and out of the device.

Means, comprising a regulating or metering valve, are disposed between the first and second fluid chambers for varying the flow of IV fluid from the first chamber into the second chamber in response to relative rotation between the upper and lower shell segments so as to thereby enable a user to selectively control the gravity flow of fluid from the first chamber into the second chamber.

The metering valve, having an axis along the longitudinal axis of the device, has a valve seat portion disposed in lower regions of the first chamber and a valve stem disposed in an upper region of the second chamber. The valve seat is formed in a conical shape and the valve stem is formed in a complementary cone shape, the valve stem being responsive to relative rotation between the upper and lower shell segments about the longitudinal axis of the device to cause the flow rate of fluid through the valve to be varied according to the rotational position of the lower shell segment relative to the upper shell segment.

At least a side wall region of said second shell segment is constructed of a transparent material so that the inside of said second chamber is visible and the flow of IV fluid through the second chamber can be seen from outside the device.

Included is a float valve disposed in the first chamber for maintaining a preestablished fluid level in the first chamber as the fluid level in the IV fluid source decreases. An opening is defined at a fluid inlet end region of the first chamber, the float valve being constructed for floating upwardly in the first chamber and blocking the opening to stop the gravity flow of fluid through the opening from the IV fluid container when the fluid level in the first chamber rises to a preestablished fluid level.

A first vent is located at an upper region of the first chamber above the preestablished fluid level for venting the first chamber to ambient pressure and a second vent is located at an upper region of the second chamber for venting the second chamber to ambient surrounding pressure.

Further included is an index mark on one of the upper and lower shell segments and a calibrated scale on the other one of the upper and lower shell segments, the scale being calibrated to indicate the rate of fluid flow from the first chamber into the second chamber.

BRIEF DESCRIPTION OF THE DRAWINGS

The present invention can be more readily understood by a consideration of the following detailed description when taken in conjunction with the accompanying drawings, in which:

FIG. 2 is a partial perspective drawing of the flow rate control device of the present invention, showing the external configuration thereof and showing the upper, inlet end of the device connected to a lower region of an exemplary IV fluid container and showing the lower, output end of the device connected to an upper end region of a patient fluid delivery tube and showing a transparent drip chamber portion of the device;

FIG. 3 is a longitudinal cross sectional view taken along line 3—3 of FIG. 2 showing the internal construction of the flow rate control device and showing a first, upper, free-floating float valve, a flow regulating valve and a second, lower, free-floating float valve for controlling and regulating fluid flow through the device;

FIG. 5 is a perspective drawing of a first variation flow rate control device having first and second chambers which are vertically movable relative to one another for regulating the flow of fluid from a first chamber into a second, drip, chamber;

FIG. 6 is a longitudinal cross sectional view taken along line 6—6 of FIG. 5, showing the internal construction of the first variation device, including a first, upper, free-floating float valve and a second, lower, free-floating float valve for fluid flow through the device;

FIG. 7 is a partial cross sectional view similar to FIG. 6, showing the second chamber of the first variation device elevated to a maximum-enabled position relative to the first chamber;

FIG. 8 is a perspective drawing of a second variation flow rate control device which is similar in many respects to the initial flow rate control device, showing the external configuration thereof and showing a flow rate scale intermediate upper and lower regions of the device, and showing an upper end of the device connected to a conventional IV fluid container and showing a lower end of the device connected to a conventional IV tube;

In the various FIGS. identical elements and features are given the same reference number and similar elements and features may be given the original reference number followed by an "a" for the first variation and by a "b" for the second variation, as will be clear from the following description.

DETAILED DESCRIPTION OF THE INVENTION

Figure 1:
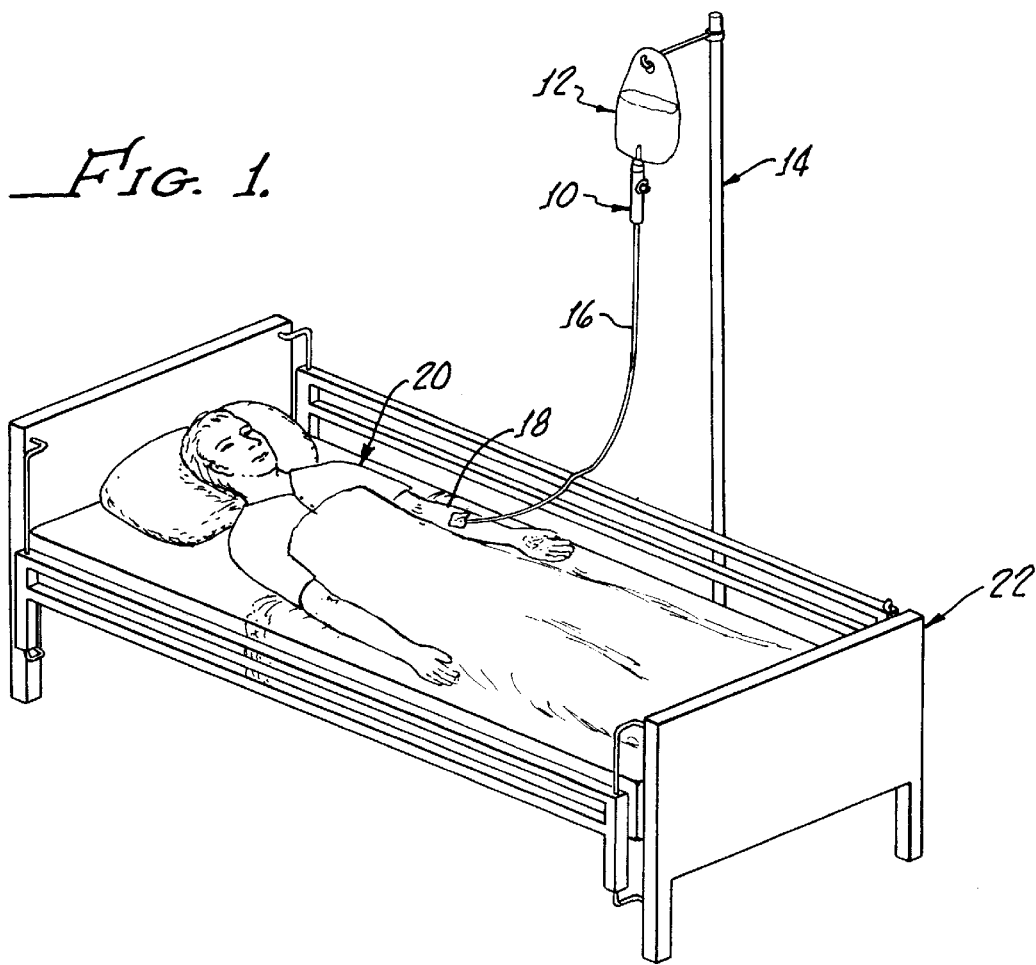
FIG. 1 is a pictorial drawing which illustrates a typical manner in which the flow rate control device of the present invention may be used to advantage, there being shown the device connected to a exemplary IV solution or fluid container and showing the output of the device being connected, through an IV tube, into the arm of a reclining patient.

In FIG. 1 there is depicted a flow rate control device or system 10, in accordance with the present invention. Device or system 10 is shown, by way of illustrative example, and as more particularly described below, connected, at an upper inlet end region, in fluid receiving relationship to a conventional IV supply source of container 12, which is depicted as being supported at an elevated level by a conventional IV stand 14. A lower end region of device 10 is shown connected in a fluid discharging relationship to the upper end of a conventional IV fluid supply conduit or tube 16 which has a lower end connected to a canula (not shown) inserted into an arm 18 of a patient 20 shown reclining on a hospital bed 22.

As shown in FIGS. 2 and 3, and as more particularly described below, flow rate control device or system 10 is externally constructed of a generally tubular upper shell segment 30, having joined to an upper end thereof a lower region 32 of a hollow inlet member 34, and a tubular lower shell segment 36, having joined to a lower end thereof an upper end region 38 of a discharge member 40. A lower end region 42 of upper shell segment 30 is joined to the upper end of lower shell segment 36 so as to form a slender, vertically-elongated and substantially closed device body 44.

As best seen from FIG. 3, an upwardly-projecting end region 46 of inlet member 34 (which is preferably constructed from a medical-grade plastic) is formed in the shape of a slender, tapered, hollow spike having a relatively sharp, beveled upper end 48 which enables fluid-flow penetration of the inlet member through a seal or plug 50 at a lower, discharge end region 52 of fluid container 12 to thereby enable the gravity flow of fluid from the container into upper segment 30.

A downwardly-extending end region 54 of discharge member 40 is formed in slender tubular shape for receiving an upper end of tube or conduit 16 to enable fluid flow from device 10 into patient 20.

As further shown in FIG. 3, internal surfaces of upper shell segment 30 and inlet member 34 largely form or define a first, upper chamber 60, and internal surfaces of lower shell segment 36 and discharge member 40 largely form or define a second, lower chamber 62.

At least regions, and preferably all, of lower shell segment 36 are formed of a transparent material, (for example, medical grade plastic such as polystyrene), so that fluid flowing through lower chamber 62 in the form of droplets 64 can be viewed and counted by a user of device 10 to obtain and/or monitor the fluid flow rate (for example, in milliliters per hour) through the device.

Shown formed integrally in lower regions of upper shell segment 30 (and more particularly described below) are fluid flow regulating means 66 which regulate the gravity flow of fluid from first, upper chamber 60 into second, lower chamber 62, and consequently through device 10.

Also as more particularly described below, first, upper, fluid flow controlling means 70 are disposed in first, upper chamber 60 for maintaining a predetermined, uniform fluid level 72 in such chamber as a level 74 of fluid 76 (FIG. 2) in container 12 changes as fluid flows from the container into and through device 10. That is, upper fluid flow controlling means 70 provide a constant fluid pressure head in device 10 regardless of the changing pressure head in fluid container 12 as fluid is drawn therefrom.

Second, lower, fluid flow controlling means 80 are disposed in second, lower chamber 62 for stopping the flow of fluid from such chamber into tube 16 when the fluid level in such chamber falls below a predetermined minimum level 82 so as to prevent the introduction of air into fluid being discharged from device 10. Second, lower, fluid flow containing means 80 are also configured, relative to the height of second chamber 62 for shutting off the flow of fluid into the lower chamber from upper chamber 60 when the fluid level in the lower chamber reaches a preestablished maximum level 84 (shown in phantom lines, FIG. 3).

An upper vent tube 90 is connected through a side wall of upper member 34 to vent upper chamber 60 to atmosphere. A conventional micropore filter element 92 is installed in filter tube 90 to maintain sterility of the upper chamber. Similarly, a lower vent tube 94, having a micropore filter element 96 is connected through a lower, side wall region of upper shell segment 30 to vent lower chamber 62 to atmosphere while maintaining sterility of the chamber.

Flow regulating means 66, as depicted in FIG. 3, comprises a generally conventional, screw-type fluid flow regulating valve which includes flow respective upper and lower, vertical fluid channels 100 and 102 formed in a lower region 104 of upper shell section 30. Fluid channels 100 and 102, which enable the flow of fluid from upper chamber 60 into upper regions of lower chamber 62 are interrupted by a valve shaft 106 having a tapered flow control section 108.

An external control knob 110 connected to a proximal end of shaft 106 enables a user to rotate the shaft so that tapered section 108 is drawn to the right. This action opens, in varying degrees, the flow path between channels 100 and 102 so as to provide a variable cross section conduit enabling the regulation of fluid flow from upper chamber 60 into lower chamber 62, to the desired or required flow rate.

A fluid flow indicating scale 112 may be provided beneath knob 110 to indicate, according to the rotational position of the knob, the approximate fluid flow rate through regulating means 66. However, the exact flow rate is ordinarily determined by a user by counting the rate at which fluid droplets 64 fall through second chamber 62. A conventional O-ring seal 114 is installed around valve stem 106 to prevent fluid leakage past the shaft and from device 10.

Figure 4:
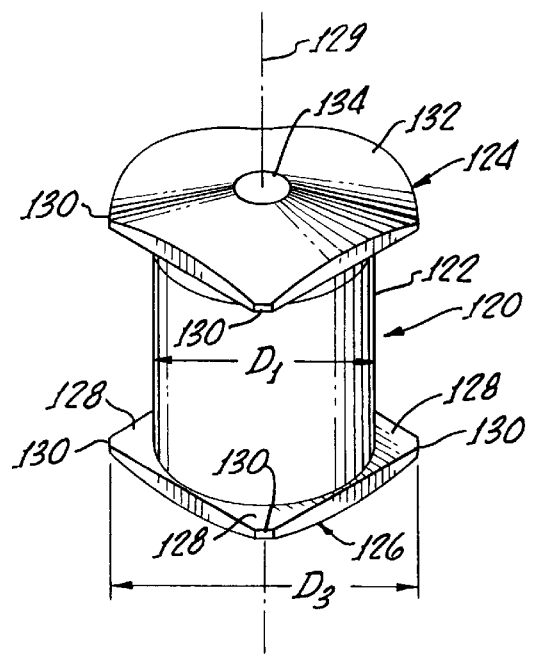
FIG. 4 is a partially cutaway perspective drawing of a representative one of the first and second free-floating float valves, showing the external configuration thereof with upper and lower end caps configured for having only minimal edge contact with their respective device chambers.

First, upper flow control means 70 comprises a buoyant first float valve 120 which is sized and configured for freely floating in a vertical direction inside of upper chamber 60. As best seen in FIG. 4, first float valve 120 comprises a light-weight, cylindrical plastic tubular body 122 having generally square, upper and lower end caps 124 and 126, respectively. The outer diameter, $D_1$, of body 122 is smaller than inner diameter, $D_2$, of upper chamber 60 (FIG. 3).

As shown for representative bottom end cap 126, all corners 128 thereof extend radially outwardly from body 112, in a symmetrical manner about a vertical axis 129 of valve 120, and terminate in short arcuate end or corner surfaces 130 which define a circle having a diameter, $D_3$, which is slightly smaller that the inside diameter, $D_2$, of upper chamber 60. Edge surfaces 130 function as guide surfaces making minimal contact with the inside of upper chamber 60 as valve 120 floats freely up and down, according to the fluid level in the chamber.

As shown in FIG. 4 for upper end cap 124, an upper surface 132 thereof is slightly convex and has a small flat circular central surface region 134 which functions as a flow-blocking surface when valve 120 floats upwardly in upper chamber 60 until such surface bears against, and blocks the gravity flow of fluid from a mating fluid orifice 136 at the lower end of a tubular downward extension 138 of spike 46 (FIG. 3).

Preferably, upper and lower valve end caps 124 and 126 are identical to one another and are joined to respective upper and lower ends of body 122 in a manner sealing first float valve 120 against fluid leaks which would affect buoyancy of the valve.

It is also preferable that second, lower flow controlling means 80 comprise a second, lower valve 140 which is identical in function, and also preferably in construction, to above-described first, upper valve 120. Lower valve 140 is free to float up and down in second chamber 62 between lower and upper preestablished fluid levels 82 and 84, respectively, according to the fluid level in the second chamber, and thereby opening and closing an outlet orifice or opening 150 at the bottom of the second chamber and an inlet orifice or opening 152 through which fluid is dropped into the second chamber.

By way of illustrative example (referring to FIG. 2), the overall length, L, of device 10 may be about 18 centimeters and the outside diameter, OD, of sections 30 and 36 may be about 2.5 centimeters, such that the combined volumes of first and second chambers 60 and 62 is about 45 milliliters. It can be appreciated that the constant fluid column height across flow control 66 is essential to the precision of fluid flow control provided by device 10.

OPERATION OF DEVICE 10

The operation of fluid flow controlling device 10 is readily apparent from the above description thereof in conjunction with associated FIGS. 1–4. Nevertheless, a brief summary of the operation of device 10 follows.

When constructed and assembled in the above-described manner, device 10 is ready for being operationally installed between fluid container 12 and fluid tube 16 into a patient 20 by inserting device spike 46 through container seal 50 and installing fluid tube 16 onto device bottom projection 54 (FIGS. 1–3).

Upon such installation (assuming that fluid is contained in container 12, that device 10 is hanging in a substantially vertical orientation as depicted in FIGS. 2 and 3, and that flow regulator valve 66 is closed) first float valve 120 will initially be resting at the bottom of first chamber 60 and second float valve 140 will be resting at the bottom of second chamber 62. As fluid flows into first chamber 60 from fluid container 12, the fluid level in the first chamber will rise, causing first float valve to float upwardly toward fluid inlet opening 136.

When the preestablished fluid level 72 is reached in first chamber 60, first float valve 120 will have floated to an elevation where upper surface region 134 of valve upper cap 124 blocks off further fluid flow into the first chamber. Flow regulator valve 66 is then opened slowly to establish the desired or required fluid flow rate from first chamber 60 into second chamber 62 (for example, by counting the number of droplets 64 falling through the second chamber over a given time interval). This flow of fluid from first chamber 60 into second chamber 62 causes the fluid level in the first chamber to fall, thereby causing first float valve 120 to float downwardly and open inlet opening 136 so that additional fluid can flow from container 12 into the first chamber until the preestablished fluid level is again reached and the first float valve again seals off fluid flow into the first chamber.

In this manner, an equilibrium situation is reached wherein as each drop of fluid flows from first chamber 60, through regulator valve 66, first float valve 120 floats down just a sufficient distance to permit a similar drop of fluid to be flowed from fluid container 12 into the first chamber before the first float valve floats back up and again shuts off the inflow of fluid from the fluid container.

Second float valve 140 in second chamber 62 functions in a reverse manner to meter fluid from the second chamber into tube 16 and on to patient 20. After initially being lifted upwardly by fluid received from first chamber 60 accumulating in lower regions of second chamber 62 to the preestablished minimum level, second float valve unblocks outlet opening 150 sufficiently to permit a drop equivalent of fluid to be discharged into tube 16. This causes a decrease in the fluid level in second chamber sufficient for second float valve to float down and reclose discharge opening 150 until the valve is relifted by a next drop of fluid dropping into the second chamber, such that each drop of fluid entering second chamber 62, a like volume is discharged therefrom into tube 16 and thence to patient 20.

If the flow of fluid from second chamber 62 into tube 16 is blocked in the tube or patient (the latter, for example, by a collapsed vein), fluid backs up in the second chamber until second valve 140 floats to the top of the chamber and cuts off the inflow of fluid until the blockage in the tube or patient is cleared.

With respect to the foregoing operation, it will be appreciated that the various preestablished fluid levels 72, 82 and 84 are selected in combination with the characteristics of the first and second float valves to cause the described operation.

VARIATION OF FIGS. 5–7

A variation fluid flow control device 10a is depicted in FIGS. 5–7. In these FIGS. 5–7, elements and features of device 10a that are identical to those described above for device 10 are given the same reference numbers. Those elements and features of device 10a which are similar or equivalent to those elements and features described above for device 10 are given the same reference numbers followed by an "a." Entirely different elements and features of device 10a are given new reference numbers.

It is to be understood that although device 10a differs in external appearance from above-described device 10, its function and operation are similar except for the construction (described below) of flow regulating means 66a.

As shown in FIGS. 5–7, device 10a comprises a first, tubular upper shell segment 30a and a second, lower tubular shell segment 36a. Upper segment 30a is constructed to form an internal first chamber 60 having a first float valve 120 disposed therein. First chamber 60 is vented to atmosphere by a vent 90. Lower segment 36a is constructed to form a second chamber 62 having a second float valve 140 disposed therein. Second chamber 62 is vented to atmosphere through a vent 94.

A tapered, tubular spike 46a at the top of upper segment 30a is provided for penetrating through a seal 50 at a lower end 52 of a fluid source 12 (FIG. 6) to permit the gravity flow of fluid through an orifice 136 at the lower end of extension 138 into first chamber 60.

Respective upper and lower segments 30a and 36a of device 10a are constructed in substantially the same manner, and function in the same way, described above, as corresponding upper and lower segments 30 and 36 of device 10.

The principal difference between device 10a and device 10 is that the gravity flow of fluid from first chamber 60 of upper segment 30a into second chamber 62 of lower segment 36a is regulated by the relative vertical position between the upper and lower segments. To this end, a flexible fluid conduit 200 is connected between a lower region of upper segment 30a and an upper region of lower segment 36a (FIGS. 5 and 6).

Flow regulating means 66a comprises a vertical support member 202 which extends downwardly from tubular region 204 at the bottom of upper segment 30a. Vertically slidingly mounted over member 202 is a slide 206 which is connected to lower segment 36a so as to extend sidewardly therefrom (FIGS. 5–7).

The relative height between upper segment 30a and lower segment 36a can be easily adjusted, to regulate the flow of fluid from first chamber 60 into second chamber 62, by sliding slide 206 (and consequently the lower segment) up or down support member 202. The effect of sliding lower segment 36a upwardly or downwardly on support member 202 actually varies the height, h, between fluid level 72 in first chamber 60 and fluid discharge opening 150 into second chamber 60.

A scale 208 may be engraved or other wise formed on support member 202 which is calibrated, for example, in milliliters per hour, to correspond to the fluid flow provided for various positions of slide 206 along the support member. As mentioned above, however, precise fluid flow rates cam best be determined by observing the drip rate of fluid through second chamber 62 (that is, by counting droplets 64 as they fall through the second chamber). Locking means 210, for example a clamp, are preferably provided for clamping slide 206 at any selected point along support member 202.

Operation of device 10a is otherwise the same as described above for device 10.

SECOND VARIATION OF FIGS. 8–10

Figure 9:
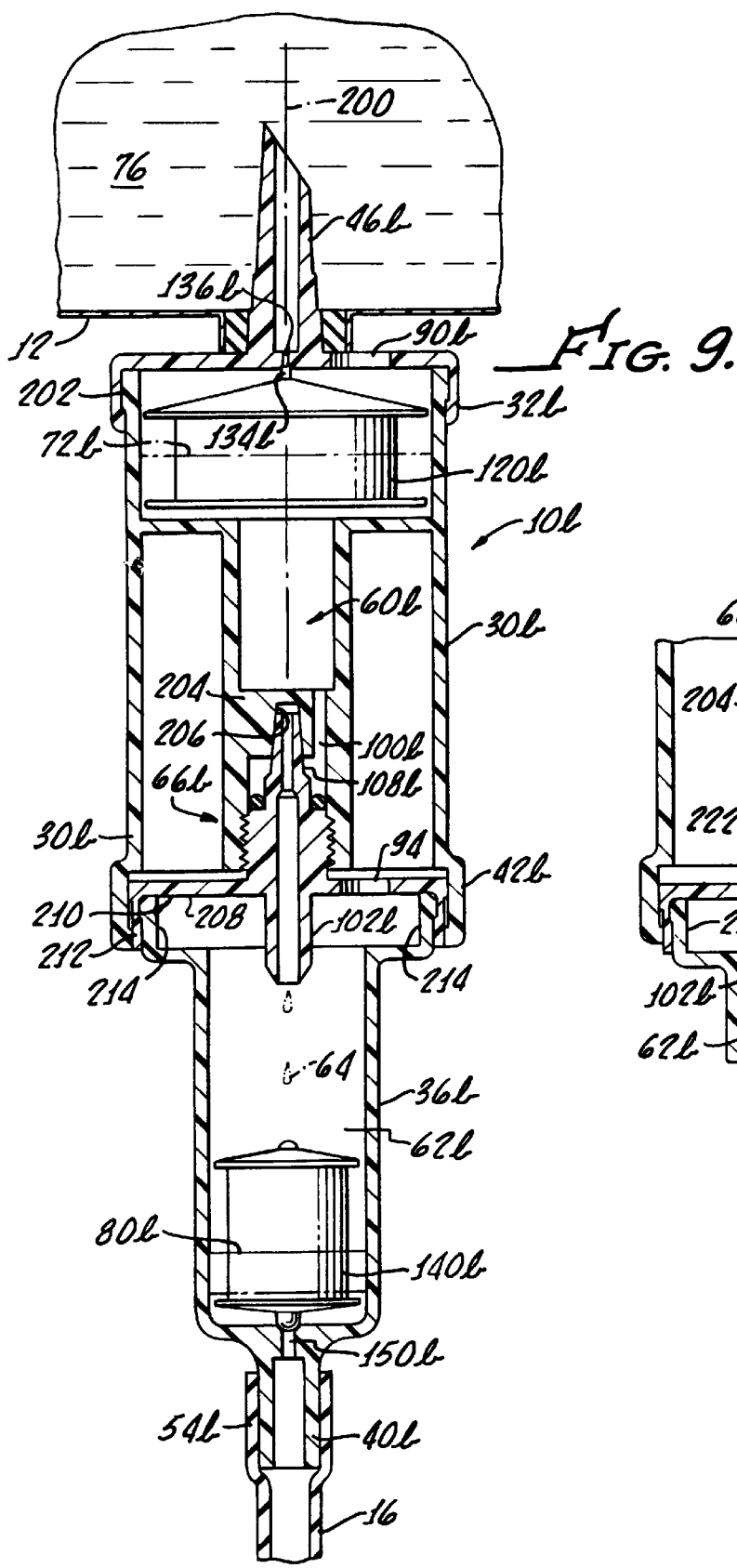
FIG. 9 is a longitudinal cross sectional drawing taken along line 9—9 of FIG. 8 showing internal construction of the second variation device and particularly showing a rotary-type flow rate control valve disposed intermediate upper and lower fluid chambers and showing the flow control valve in a closed condition.
Figure 10:
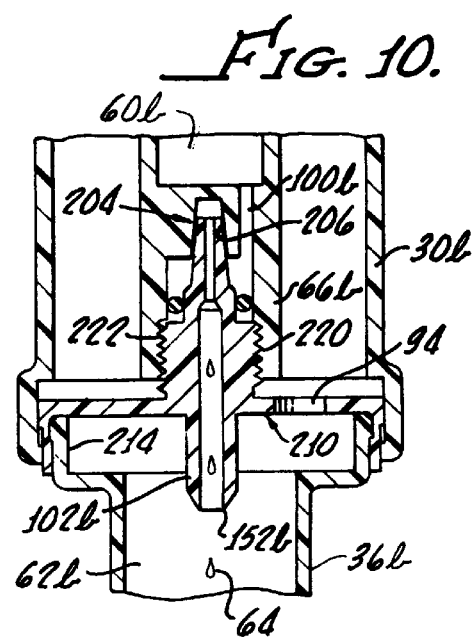
FIG. 10 is a partial longitudinal cross sectional drawing in the plane of FIG. 9 and showing the flow control valve in a partially open condition.

A second variation fluid flow control device 10b is depicted in FIGS. 8–10. In these FIGS. 8–10, elements and features of second variation device or system 10b that are identical to those described above for device 10 are given the same reference numbers. Those elements and features of device 10b which are similar or equivalent to those elements and features described above for device 10 are given the same reference numbers followed by a "b." Entirely different elements and features of device 10b are given new reference numbers.

As more particularly described below, second variation flow rate control device 10b, as is shown in FIGS. 8 and 9, is connected, at an upper inlet end region, in fluid receiving relationship to a conventional IV supply source or container 12 which forms no part of the present invention, Container 12 (which may be a flexible plastic IV solution bag) is ordinarily hung in the manner shown in FIG. 1 (relative to device 10) from an IV stand 14.

A lower end region of device 10b is connected in fluid discharge relationship to the upper end of a conventional IV fluid supply conduit or tube 16. In the same manner depicted above in FIG. 1 with respect to device 10, tube 16 has a lower end connected to a canula (not shown) for insertion into a patient (corresponding to patient 20 depicted in FIG. 1) to which IV fluid from container 12 is gravity flowed in a controlled manner through device 10b.

As further shown in FIGS. 8 and 9, flow rate control device 10b is constructed of respective upper and lower shell segments 30b and 36b, both of which are generally cylindrical in external appearance and both of which are constructed of a medical grade of plastic. As described below, upper and lower shell segments 30b and 36b are snap-fit together in a manner permitting relative rotation between the two shell segments about a longitudinal axis 200 of device 10b.

As shown in FIG. 9, a peripheral, downwardly-extending flange 32b of a hollow inlet member 34b is tightly snap fit onto the outside of an upper end protruding ramp 202 of upper shell segment 30b. An upwardly extending, hollow spike 46b of inlet member 34b enables penetration into IV container 12 to thereby permit fluid 76 in the container to flow under gravity into device 10b.

At the bottom of device 10b, IV tube 16 is connected in a conventional manner, for example, by a leur fitting configuration, to a downwardly-extending end 54b of lower end region 40b of lower shell segment 36b. This connection permits flow-regulated fluid to flow from device 10b into tube 16 and from there into the patient to which the discharge end of the tube is connected.

Defined inside of upper shell segment 30b is a generally T-shaped first or upper fluid chamber 60b having an upper opening or orifice 136b through which fluid from container 12 flows through spike 46b (into the chamber (FIG. 9). Fluid flow from container 12 into first chamber 60b through orifice 136b is controlled by a first float valve 120b installed in the first chamber. First float valve 120b is constructed and operates in a manner to maintain a fluid level 72b in first chamber 60b in the same manner described above for first float valve 120 in first chamber 60 of device 10. Thus, as the fluid level in first chamber 120b starts to fall below level 72b (by the flowing of fluid from the first chamber as described below), first float valve 120b starts floating down in the first chamber, thereby moving an upper central plug region 134b of the first float valve downwardly out of fluid sealing relationship with fluid opening 136b. Such downward movement of first float 120b enables fluid from container 12 to flow into first chamber 120b, thereby increasing the fluid level in the first chamber and causing first float valve 120b to float up until plug region 134b seals off opening 136b and stops the flow of fluid into the first chamber. It is to be appreciated that this action occurs on a continual, virtually microscopic level, while device 10b is delivering small quantities of IV fluid from container 12 to the patient to whom tube 16 is connected.

Defined inside of lower shell segment 36b is a generally cylindrical second or drip chamber 62b which is connected for receiving fluid from first chamber 60b and for discharging fluid from a lower opening or passageway 150b into tube 16.

To this end, when upper and lower shell segments 30b and 32b are connected together, lower regions of first chamber 60b are in gravity fluid flow communication with upper regions of second chamber 62b through a passageway 100b that is parallel to axis 200 (FIGS. 9 and 10). The rate at which fluid flows into second chamber 62b from first chamber 60b is controlled by a fluid flow regulator or control means or assembly 66b (described below) through which the fluid flows and out through a tubular portion 102b of the regulator means or assembly.

A second float valve 140b is disposed in second chamber 62b for controlling the flow of fluid out of the second chamber. Second float valve 140b is constructed and operates in the same manner as second float valve 140 of device 10 described above. When fluid is flowing through control or regulator means 66b into second chamber 62b from first chamber 60b, second float valve 140b floats at a level so as to establish and maintain a normal fluid level 80b in the second chamber.

If the flow of fluid from second chamber 62b increases appreciably (for example, if the patient lowers the arm into which the IV fluid is delivered from device 10b), fluid starts to drain out of the second chamber, through opening 150b, faster than fluid flows into the second chamber from first chamber 60b, thereby reducing the fluid level in the second chamber. Second float 140b follows the fluid level down with the decreasing fluid level in the second chamber until a lower region of the float valve closes off discharge opening 150b. As the fluid discharge from second chamber 62b returns to normal, the fluid level in the second chamber rises, floating second float valve 140b up from a sealing-off relationship with opening 150b, thereby reestablishing flow from device 10b to the patient.

On the other hand, if fluid flow through tube 16 is slowed down (for example, by the patient elevating the arm receiving fluid from device 10b), the fluid level in second chamber 62b rises, thereby floating up second float valve 140b. If the fluid discharge is sufficiently restricted, the fluid level in second chamber 62b rises until an upper surface of second float valve 140b seals off a fluid entry opening 152b in tubular portion 102b, thereby stopping the flow of fluid into the second chamber.

Fluid flow regulator or control means or assembly 66b comprises, as shown in FIGS. 9 and 10, a valve having a body portion 204 with a tapered or cone-shaped valve seat 206 which diverges in a downward direction and which is coincident with longitudinal axis 200 of device 10b. Valve body portion 204 is shown formed as part of upper shell portion 30b at the bottom of first chamber 60b. Passageway 100b mentioned above, passes through valve body portion 204 to one side of valve seat 206.

An upwardly extending, conical valve stem portion 108b of valve or regulator assembly 66b is formed having an axial aperture 207 extending axially therethrough and is part of a separate member 208 of device 10b. Member 208 has a disc-shaped region 210 with a downwardly extending annular flange 212 which tightly snaps over an upper end region 214 of lower shall segment 36b in the manner described above for portion 34b.

As described above, and as illustrated in FIGS. 9 and 10, valve body portion 204 with valve seat 206 is formed as part of upper shell segment 30b and valve stem portion 108b of regulator assembly or means 66b is attached, by disc portion 108 to lower shell segment 36b. A male threaded region 220 formed on valve stem portion 108b mates with a female threaded region 222 of valve body portion 204 so that relative rotation between upper and lower shell segments 32b and 36b moves the valve stem into or out of valve seat 206, according to the direction of relative rotation, so as to control or regulate the flow of fluid into second drip chamber 62b from first chamber 60b. A conventional O-ring 224 is installed around stem portion 108b to prevent fluid leakage past the threaded region of the valve.

Fluid flow from first chamber 60b into second chamber 62b is through passageway 100b, upwardly through the annular space between valve seat 206 and valve stem 108b and then downwardly through aperture 207. From opening 152b, the fluid falls in droplets 64 onto second float valve and hence into second chamber 62b.

To enable relative rotation between upper and lower shell segments 30b and 36b, a lower region 42b of the upper segment snaps over flange region 212 of disc 208 in a manner describe above for cap 34b and upper shell segment 30b, except that such interconnection is not so tight but that rotational movement is permitted between the upper and lower shell segments. In addition, the interconnection between upper and lower shell segments 30b and 36b is constructed to enable limited axial movement between the two shell segments. As is needed to enable valve stem 108b to be threaded into and out of valve body 204, as described above.

Although the interconnection between upper and lower segments 30b and 36b is made not so tight as to enable relatively easy relative rotation between the two segments, the interconnection is sufficiently tight to retain any selected relative rotation against unintentional relative rotation.

As shown in FIG. 8, an index mark 230 is formed on the outside of lower shell segment 36b just below region 42b of upper shell segment 30b. Marked around the outside of upper shell segment region 42b is a flow rate scale 232 that is calibrated against the actual fluid flow rate from first chamber 60b into second chamber 62b, as determined by counting the number of droplets 64 per minute as observed through the transparent region of lower shell segment 36b.

Since there are some advantages of forming left-hand threads 220 and 222, scale 232 is depicted in FIG. 8 as an increasing flow rate (for example, in milliliters per hour) for clockwise rotation of lower shell segment 36b relative to upper shell segment 32b. Thus for left-hand threads, the flow rate of fluid through device 10b is increased by relative clockwise rotation of supper and lower segments 32a and 36a and the fluid rate is decreases by counter clockwise relative rotation of the two segments.

It will, of course, be understood that device 10b can alternatively be formed with right-hand threads, in which case the fluid flow through the device will be increased by counterclockwise relative rotation and decreased by relative clockwise rotation. Also, in such case, the direction of calibration of scale 232 would be reversed.

To assure proper gravitational flow of IV fluid through device 10b, upper chamber 60b is vented to the ambient surroundings though a conventional, disc-shaped hydrophobic microfilter 90b (FIGS. 8 and 9). Similarly, lower chamber 66b is vented by a disc-shaped hydrophobic microfilter 94b.

Operation of device 10b is simple and efficient, the flow through the device being set or regulated by relative rotation between upper and lower shell segments 30b and 36b, according to calibration scale 232. Device 10b has the further advantage that all parts snap together, thereby making fabrication and assembly inexpensive.

Although there have been described and illustrated a fluid flow control device (especially adapted for controlling the flow of IV fluid), and variations thereof having a constant fluid head and variable flow control orifice or variable fluid head and a fixed size flow control orifice provision, in accordance with the present invention for purposes of illustrating the manner in which the invention may be used to advantage, it is to be appreciated that the invention is not limited thereto. Therefore, any and all variations and modifications that may occur to those skilled in the applicable art are to be considered as being within the scope and spirit of the claims as appended hereto.

What is claimed is:

1. A gravity flow IV fluid flow device with constant fluid head provision, said device comprising:
  a. an upper shell segment having an upper end region configured for receiving a flow of IV fluid from an external IV fluid source;
  b. a lower shell segment having a lower end region configured for discharging said flow of IV fluid from said device, a lower region of said upper shell segment being connected to an upper region of said lower shell segment for relative rotation between the upper and lower shell segments and for limited axial movement between the upper and lower shell segments;
  c. a first, upper fluid chamber defined inside said upper shell segment;
  d. a second, lower fluid chamber defined in said lower shell segment, said second fluid chamber being in fluid flow communication with said first, upper chamber;
  e. a fluid flow regulating valve disposed between said first and second fluid chambers, said fluid flow regulating valve being configured for varying the flow of fluid from the first chamber into the second chamber in response to relative rotation between the upper and lower shell segments, said valve including a valve seat portion disposed in said upper shell segment at the bottom of said first chamber and a valve stem disposed in an upper region of said second shell segment at the top of said second chamber, said valve seat being formed in a conical shape and said valve stem being formed in a complementary cone shape, and wherein the valve stem is responsive to relative rotation by a user between the upper and lower shell segments about the longitudinal axis of said device after assembly of said device to cause the flow rate of fluid through said valve to be varied according to the rotational position of the lower shell segment relative to the upper shell segment so as to thereby enable a user to selectively control the gravity flow of fluid from said first chamber into said second chamber without any disassembly of the device, said upper shell segment connection to said lower shell segment limiting axial movement between the upper and lower shell segments to the amount of axial adjustment of said fluid flow regulating valve;

f. a first float valve disposed in said first chamber for maintaining a preestablished fluid level in said first chamber as the fluid level in said IV fluid source decreases, and including an opening at a fluid inlet end region of the first chamber, and wherein said first float valve is constructed for floating upwardly in said first chamber and blocking said opening to stop the gravity flow of fluid through said opening from the IV fluid container when the fluid level in said first chamber rises to a preestablished fluid level.

2. The gravity flow fluid flow device as claimed in claim 1, wherein at least a side wall region of said second shell segment is constructed of a transparent material so that the inside of said second chamber is visible and the flow of IV fluid through the second chamber can be seen from outside the device.

3. The gravity flow fluid flow device as claimed in claim 1, including a first vent located at an upper region of said first chamber above said preestablished fluid level for venting the first chamber to ambient pressure, and a second vent located at an upper region of said second chamber for venting the second chamber to ambient surrounding pressure.

4. The gravity flow fluid flow device as claimed in claim 1, including an index mark on one of the upper and lower shell segments and including a calibrated scale on the other one of the upper and lower shell segments, said scale being calibrated to indicate the rate of fluid flow from the first chamber into the second chamber.

5. A gravity flow IV fluid flow device with constant fluid head provision, said device comprising:

a. an upper shell segment having an upper end region configured for receiving a flow of IV fluid from an external IV fluid source;

b. a lower shell segment having a lower end region configured for discharging said flow of IV fluid from said device, a lower region of said upper shell segment being connected to an upper region of said lower shell segment for relative rotation between the upper and lower shell segments and for limited axial movement between the upper and lower shell segments;

c. a first, upper fluid chamber defined inside said upper shell segment;

d. a second, lower fluid chamber defined in said lower shell segment, said second fluid chamber being in fluid flow communication with said first, upper chamber;

e. a fluid flow regulating valve disposed between said first and second fluid chambers, said fluid flow regulating valve being configured for varying the flow of fluid from the first chamber into the second chamber in response to relative rotation between the upper and lower shell segments, said valve including a valve seat portion disposed in said upper shell segment at the bottom of said first chamber and a valve stem disposed in an upper region of said second shell segment at the top of said second chamber, said valve seat being formed in a conical shape and said valve stem being formed in a complementary cone shape, and wherein the valve stem is responsive to relative rotation by a user between the upper and lower shell segments about the longitudinal axis of said device after assembly of said device to cause the flow rate of fluid through said valve to be varied according to the rotational position of the lower shell segment relative to the upper shell segment so as to thereby enable a user to selectively control the gravity flow of fluid from said first chamber into said second chamber without any disassembly of the device, said upper shell segment connection to said lower shell segment limiting axial movement between the upper and lower shell segments to the amount of axial adjustment of said fluid flow regulating valve;

f. a first float valve disposed in said first chamber for maintaining a preestablished fluid level in said first chamber as the fluid level in said IV fluid source decreases, and including an opening at a fluid inlet end region of the first chamber, and wherein said first float valve is constructed for floating upwardly in said first chamber and blocking said opening to stop the gravity flow of fluid through said opening from the IV fluid container when the fluid level in said first chamber rises to a preestablished fluid level; and g. a second float valve disposed in said second chamber for maintaining a preestablished fluid level in said second chamber, and including an outlet opening at a fluid outlet end region of the second chamber, and wherein said second float valve is constructed for floating downwardly in said second chamber and blocking said outlet block said outlet opening when the fluid level in said second chamber falls to a preestablished fluid level.

* * * * *